United States Patent [19]

Duhamel et al.

[11] 4,200,102

[45] Apr. 29, 1980

[54] BABY HYGIENIC RECEPTOR

[76] Inventors: Ernest Duhamel; Fernando Poirier, both of 1235 Debullion, Apt. 10, Montreal, Canada, H2X-1K9

[21] Appl. No.: 878,313

[22] Filed: Feb. 16, 1978

[51] Int. Cl.² .................................................. A61F 5/44
[52] U.S. Cl. ........................................ 128/286; 128/295
[58] Field of Search ........................ 128/286, 288, 295

[56] References Cited

U.S. PATENT DOCUMENTS

| 660,388 | 10/1900 | Moberg et al. | 128/295 |
|---|---|---|---|
| 913,983 | 3/1909 | Scheller et al. | 128/286 |
| 924,337 | 6/1909 | Frommann | 128/286 |
| 976,883 | 11/1910 | Keagy et al. | 128/286 |
| 1,329,195 | 1/1920 | Martinka | 128/286 |
| 3,316,911 | 5/1967 | Barr | 128/286 |
| 3,532,093 | 10/1970 | Lovret | 128/286 |

*Primary Examiner*—Robert W. Michell
*Assistant Examiner*—C. W. Shedd
*Attorney, Agent, or Firm*—Howard I. Podell

[57] ABSTRACT

An hygienic prosthesis or diaper for a baby comprising a kidney-shaped body having a pair of spaced containers for receiving urine and excrement. Each container has an inlet and an outlet. The inlets close around the human orifices to form seals. The outlets are adapted for connection to an aspirating pump for emptying and can be washed with an antiseptic solution. A harness is secured to the upper part of the body and fits around the waist with the lower part of the body being secured to the back of the harness.

2 Claims, 4 Drawing Figures

BABY HYGIENIC RECEPTOR

FIELD OF THE INVENTION

This invention relates generally to a novel diaper-like article which can be evacuated and flushed.

DESCRIPTION OF THE PRIOR ART

The prior art, as exemplified by U.S. Pat. No. 3,316,911; 976,883; 1,329,195; 924,337 and 913,983 is generally illustrative of the pertinent art but the aforementioned patents are non-applicable to the present invention. While the prior art expedients are generally acceptable for their intended purposes only, they have not proven entirely satisfactory in that they are either complex and expensive to manufacture, or bulky and inconvenient to use. As a result of the shortcomings of the prior art, typified by the above, there has developed a substantial need for improvement in this field.

The principal object of this invention is to provide a device or article of this character which combines simplicity, strength and durability in a high degree, together with inexpensiveness of construction so as to encourage widespread use thereof.

Other objects of this invention will in part be obvious and in part hereinafter pointed out.

The invention accordingly consists in the features of construction, combinations of elements, and arrangement of parts which will be exemplified in the construction hereinafter described, and of which the scope of application will be indicated in the following claims.

SUMMARY OF THE INVENTION

This invention resides in an hygienic prosthesis or diaper for a baby comprising a kidney-shaped body having a pair of spaced containers for receiving urine and excrement. Each container has an inlet and an outlet. The inlets close around the human orifices to form seals. The outlets are adapted for connection to an aspirating pump for emptying and can be washed with an antiseptic solution. A harness is secured to the upper part of the body and fits around the waist with the lower part of the body being secured to the back of the harness.

BRIEF DESCRIPTION OF THE DRAWING

In the accompanying drawing, in which is shown one of the various possible illustrative embodiments of this invention, wherein like reference character identify the same or like parts.

DESCRIPTION OF THE PREFERRED EMBODIMENT

Figure 1:
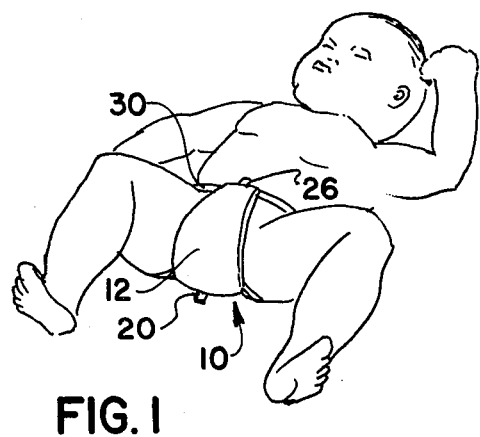
FIG. 1 is a view in perspective showing the article of the invention being worn.
Figure 2:
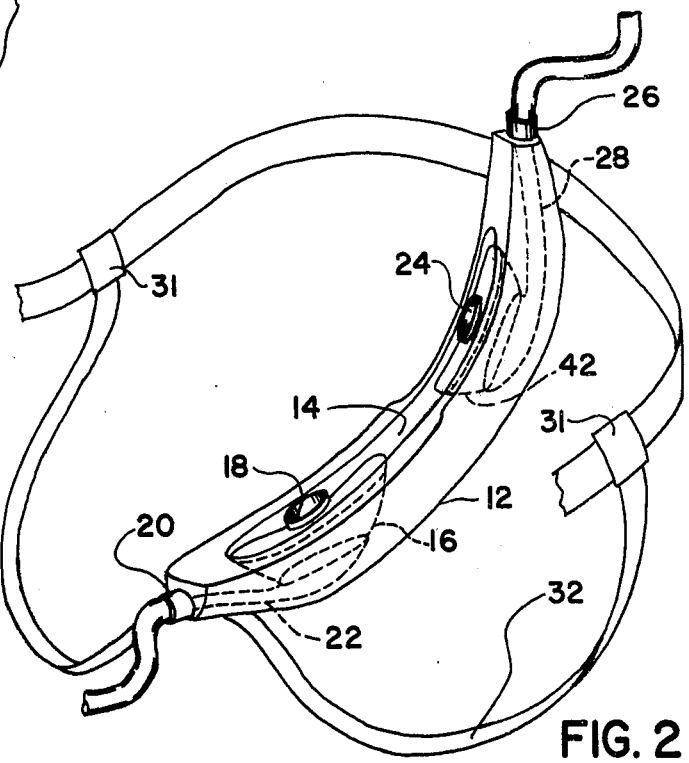
FIG. 2 is a side elevation partly in section thereof.
Figure 3:
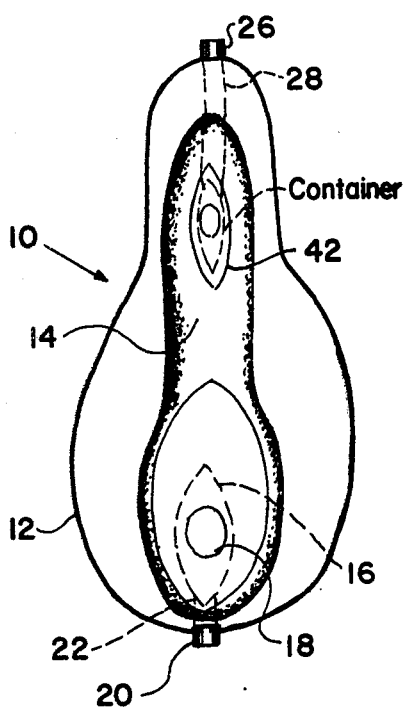
FIG. 3 is a top plan view thereof.
Figure 4:
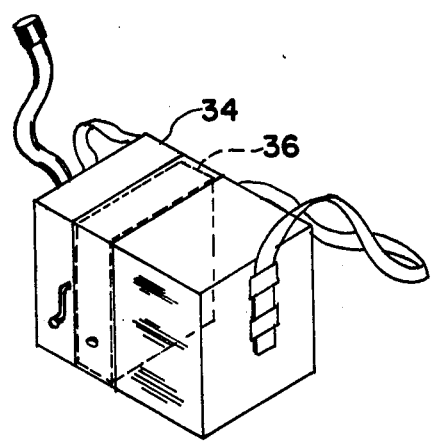
FIG. 4 is a perspective view of a pump and rinse liquid container bag for use along with the article of the invention.

With reference to the drawing, there is shown and illustrated a novel diaper constructed in accordance with the principles of the invention and designated generally by reference character 10. The illustrated tangible embodiment of the invention includes an air-filled generally kidney-shaped body 12 of nylon, non-rigid vinyl plastic or the like which has a concave cavity 14 along its center. A first container 16 for excrement is positioned in the lower end of body 12 and has inlet 18 which is adapted to contact the rectal area. Container 16 has an outlet 20 at the end of tube 22 which is connected to container 16.

The upper part of body 12 holds urine container 42 which has inlet opening 24 adapted to contact the urinary organs. Container 42 is connected to an outlet 26 by tube 28. An elastic strap 30 is secured near the upper part of body 12 for fastening around the baby's waist. A second belt 32 is secured at its midpoint to the upper face of the lower part of body 12 and is secured in harness fashion in the back to belt 30 by suitable fasteners 31 such as mating Velcro ® bands.

Outlets 20 and 26 are adapted to be connected to a manual pump 34 in a bag 36. Bag 36 also holds a rinse liquid container for pouring antiseptic solution through the containers after they have been evacuated.

The present article solves the problem of having to wash or throw away diapers. Advantageously, it can be flushed without being removed. It needs to be taken off only once a day but should be flushed two or three times a day. It is safe, flexible, compact and leaves all liberty of movement to the baby.

In larger sizes, the article of the invention can be used on adults after major surgery.

The operation and use of the invention hereinabove described will be evident to those skilled in the art to which it relates from a consideration of the foregoing.

It will thus be seen that there is provided a device in which the several objects of this invention are achieved, and which is well adapted to meet the conditions of practical use. Its advantages are easily seen.

It is thought that persons skilled in the art to which this invention relates will be able to obtain a clear understanding of the invention after considering the foregoing description in connection with the accompanying drawing. Therefore, a more lengthy description is deemed unnecessary.

It is to be understood that various changes in shape, size and arrangement of the elements of this invention as claimed may be resorted to in actual practice, if desired.

Having thus described the invention, what is claimed as new and to be secured by Letters Patent is:

1. A reusable diaper including a generally kidney-shaped body; said body having upper and lower portions with connecting straps adapted to fit around the body of a wearer; an elongated concave cavity along the inside of said kidney-shaped body adapted to contact the perineal regions of a wearer; a first excrement container in said body having inlet and outlet means; a second container spaced from said first container and having inlet and outlet means; each said outlet means being independently connectable to a pump for evacuation and for rinsing, said inlet means being ovate ducts extending from said elongated cavity to each of said containers, said duct for said first container is sized and spaced from said second container so as to be aligned with the rectum of the wearer of the device when the inlet duct for said second container is aligned with the urinary organ of the wearer.

2. The invention as recited in claim 1, wherein said body includes tubes connecting said outlets to said containers.

* * * * *